(12) United States Patent
Rex

(10) Patent No.: US 6,517,730 B1
(45) Date of Patent: Feb. 11, 2003

(54) METHOD AND APPARATUS FOR WAFER SANITIZATION

(75) Inventor: Hans Rex, West Wallsend (AU)

(73) Assignee: Aquagem Holdings Pty Limited, The Junction (AU)

( * ) Notice: Subject to any disclaimer, the term of this patent is extended or adjusted under 35 U.S.C. 154(b) by 0 days.

(21) Appl. No.: 09/623,321

(22) PCT Filed: Mar. 5, 1999

(86) PCT No.: PCT/AU99/00137

§ 371 (c)(1), (2), (4) Date: Oct. 16, 2000

(87) PCT Pub. No.: WO99/44949

PCT Pub. Date: Sep. 10, 1999

(30) Foreign Application Priority Data

Mar. 5, 1998 (AU) .............................................. PP2161

(51) Int. Cl.[7] .............................. C02F 1/50; C02F 1/72; C02F 1/76
(52) U.S. Cl. ........................ 210/759; 422/37; 210/764; 210/753; 210/754
(58) Field of Search ................... 422/37, 122; 210/753, 210/754, 759, 764; 252/175, 181

(56) References Cited

U.S. PATENT DOCUMENTS 5,858,246 A * 1/1999 Rafter ........................ 210/754

FOREIGN PATENT DOCUMENTS

| AU | 657897 | * 3/1995 |
| WO | WO 97/34834 | 9/1997 |
| WO | WO 98/22397 | 5/1998 |

* cited by examiner

Primary Examiner—Robert J. Warden, Sr.
Assistant Examiner—Sean E. Conley
(74) Attorney, Agent, or Firm—Timothy J. Keefer; Wildman, Harrold, Allen & Dixon

(57) ABSTRACT

Apparatus is described for sanitizing a flow of water recirculated from a body of water such as a swimming pool by a pump (16) having an inlet conduit (10) and an outlet conduit (18) both in fluid communication with the body of water. The apparatus comprises a container (22) which is adapted to hold sources of silver and copper metal and halogen reagent which, under the action of oxidising agents forms colloidal dissolved metals. Metering means (12) is adapted to deliver hydrogen peroxide reagent into the inlet conduit (10). Water is pumped from outlet conduit (18) through feed conduit (20) which is connected to the container (22) and then through return conduit (24) which connects to either inlet conduit (10) or the outlet conduit (18) to a position upstream of the connection of the feed conduit (10) to the outlet conduit (18). The amount of hydrogen peroxide and halogen added are predetermined by the volume of water to be sanitized. The amount of hydrogen peroxide is predetermined to ensure that all halogen present is converted to hypochlorous acid and sufficient hydrogen peroxide is left over to provide at least some oxygenation of the water.

9 Claims, 2 Drawing Sheets

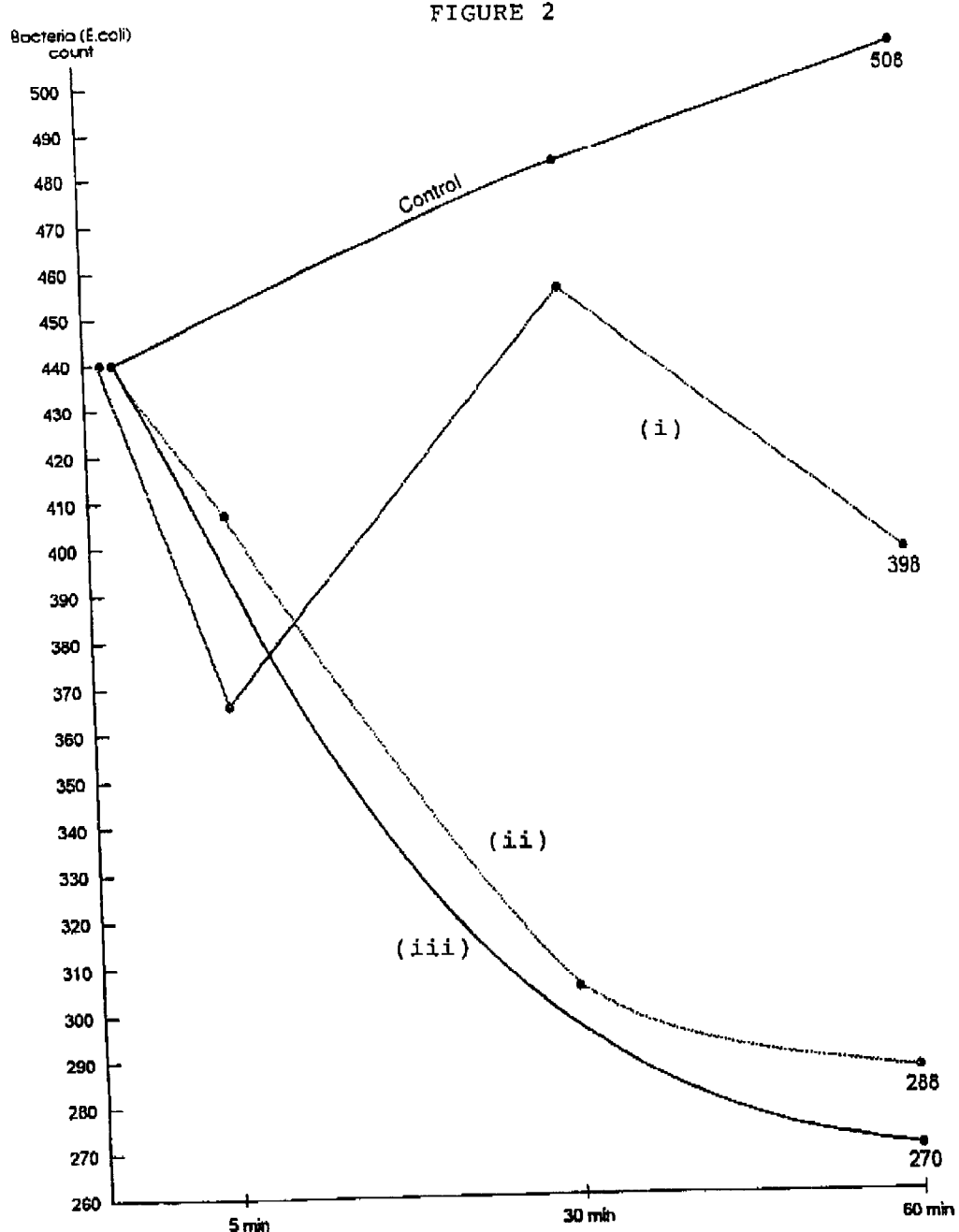

METHOD AND APPARATUS FOR WAFER SANITIZATION

FIELD OF THE INVENTION

The present invention relates to a method and apparatus for water sanitisation. The invention will primarily be described with reference to its use to provide sanitisation of swimming pool water containing bacteria, algae and other water-borne diseases, but it should be remembered that the invention can have broader applications to any other body of water which may contain such organisms and diseases and which therefore require sanitisation.

CROSS REFERENCE TO RELATED APPLICATION

This application claims the priority of Australian patent application Serial No. PP 2161 filed on Mar. 5, 1998.

BACKGROUND ART

Although chlorine and other halogens are the preferred method of water sanitisation, it is well known that this method has a number of drawbacks. "Superchlorination" of pools (where the concentration of chlorine in solution exceeds 10 ppm) is scientifically the recommended requirement to sanitise water to meet the requirements of health regulations even though all halogens, and especially so chlorine, are highly reactive elements and readily form by-products, which themselves can be known dangerous environmental pollutants and proven carcinogens. Chlorine itself is highly toxic for human beings, and health authorities only permit certain levels of chlorine in swimming pool water (typically 2–3 ppm). Consumption or degradation of the chlorine through normal usage of the swimming pool can cause a breakdown in the effectiveness of the sanitisation process. In summary, current methods of sanitisation using halogens alone are crude, not fully successful at eliminating disease organisms, and highly dangerous from an occupational health standpoint since the reagents used for effective sanitisation are extremely toxic.

Chlorine forms hypochlorous acid with water under certain circumstances. It is well known that approximately 80% of available chlorine ions are converted to hypochlorous acid if the water pH is around 6.8. At a water pH of around 8.0 only 20% of the available chlorine is converted to hypochlorous acid.

Hypochlorous acid is approximately 300 times more effective as a sanitiser than chlorine, and it does not form dangerous by-products. For instance, it is known that hydrogen peroxide is a natural product of human body cells. In combination with available chlorine (from body salt intake), the hydrogen peroxide will form hypochlorous acid, constituting a disease control mechanism in the cell environment.

Hypochlorous acid formation by means of addition of chlorine and hydrogen peroxide reagents is thus much more environmentally friendly and less dangerous to the users of swimming pools than other materials used for sanitisation such as chlorine, bromine and iodine. Concentrations of hypochlorous acid can be kept at relatively high levels giving better health protection for users of the swimming pool. It has become usual to identify a preferred operating range of redox potential (ORP) for the water being sanitised of 220–290 mV, more preferably 235–275 mV when the correct relative amounts of hydrogen peroxide and halogen are present.

All of the abovementioned features have been disclosed in our Australian Patent AU657897. Currently, health authorities worldwide are seeking methods to realize even lower concentrations of disease-causing organisms and means to keep bacteria under control more effectively with minimum exposure of water users to halogen reagents, combined with effective conversion of hydrogen peroxide and halogens to hypohalous acid.

Although the use of ionic species such as copper and silver salt ions are known concomitant additives to improve the performance of a water sanitisation process using a hydrogen peroxide and chlorine, as disclosed in WO 98/22397, such systems rely on the release of dangerous toxins into water systems, such as $Cu^{2-}$ ions, along with high concentrations of chlorine released locally into the water body in the vicinity of the additive pellets described therein. Ions such as $Cu^{2-}$ ant $Ag^-$ are very poisonous to living creatures including man. Direct release of such species into a water system in an essentially uncontrolled manner can be unsafe practice, both for water users and a dangerous procedure for operators.

SUMMARY OF THE INVENTION

The present invention in a first aspect provides a method of sanitising a body of water by:

(a) adding an amount of hydrogen peroxide predetermined by the volume of water to be sanitised, and (b) adding an amount of halogen predetermined by the volume of water to be sanitised, and (c) adding an amount of one or more of the group comprising silver and copper as colloidal dissolved metals produced by the controlled dissolution of the corresponding metallic source metals under the action of hydrogen peroxide and halogen present in the water to be sanitised, and (d) wherein the amount of hydrogen peroxide is so predetermined to ensure that all halogen is converted to hypohalous acid and sufficient hydrogen peroxide is left over to provide at least some oxygenation of the water.

Preferably the water sanitisation method includes the use of a reticulation pump for providing a flow of water requiring sanitisation, and a container arranged to receive water under pressure from said pump, said container being adapted to contain sources of said colloidal dissolved metals and halogen reagent, whereby said water is recirculated through said container and returned to the flow of water, and wherein, upstream from where said container receives water from said pump, metering means are arranged to deliver hydrogen peroxide reagent into the flow of water.

Preferably the water sanitisation method provides for said water to be returned to the flow of water downstream of the delivery of hydrogen peroxide reagent into the flow of water.

Preferably the water sanitisation method provides for the flow of water to said container from the pressure side of the pump to be regulated by constriction in order to allow an appropriate residence time of fluid in the container for effective chemical reactions to occur.

Preferably the water sanitisation method provides for the rate of hydrogen peroxide reagent delivery to be adjusted to suit the particular conditions of sanitisation required and the flow rate of water for treatment.

In a further aspect, the present invention provides apparatus for sanitising a flow of water recirculated from a body of water by a pump having an inlet conduit and an outlet conduit both in communication with the body of water, said apparatus comprising a container adapted to hold sources of one or more of the group comprising silver and copper as colloidal dissolved metals and a source of halogen reagent, a feed conduit extending from the container and adapted to be connected to the outlet conduit, a return conduit adapted to be connected to one of the inlet conduit and the outlet conduit, such that in use water under pressure from the pump passes through the feed conduit, the container, and the return conduit, said apparatus further comprising metering means adapted to deliver hydrogen peroxide reagent into the flow of water upstream of the connection of the feed conduit to the outlet conduit.

Preferably the apparatus for sanitising water has metering means comprising a solenoid valve or metering pump or the like, adapted to deliver hydrogen peroxide reagent at a pre-determined rate into the flow of water upstream of the pump.

Preferably the apparatus for sanitising water has a pump associated with a coarse filter, wherein the return conduit is connected to the inlet conduit upstream of the coarse filter.

Preferably the apparatus for sanitising water has a container adapted to include sources of metallic copper and silver and halogen reagent in which the metallic copper and silver are present as a plurality of metallic bars, rods or granules, and sources of chloride are present in solid form.

BRIEF DESCRIPTION OF THE DRAWINGS

Notwithstanding any other forms which may fall within the scope of the present invention, a preferred form of the invention will now be described, by way of example only, with reference to the accompanying drawing in which:

FIG. 2 shows a graphical representation of the experimental results obtained using a water sanitisation process in accordance with the invention.

MODES FOR CARRYING OUT THE INVENTION

Figure 1:
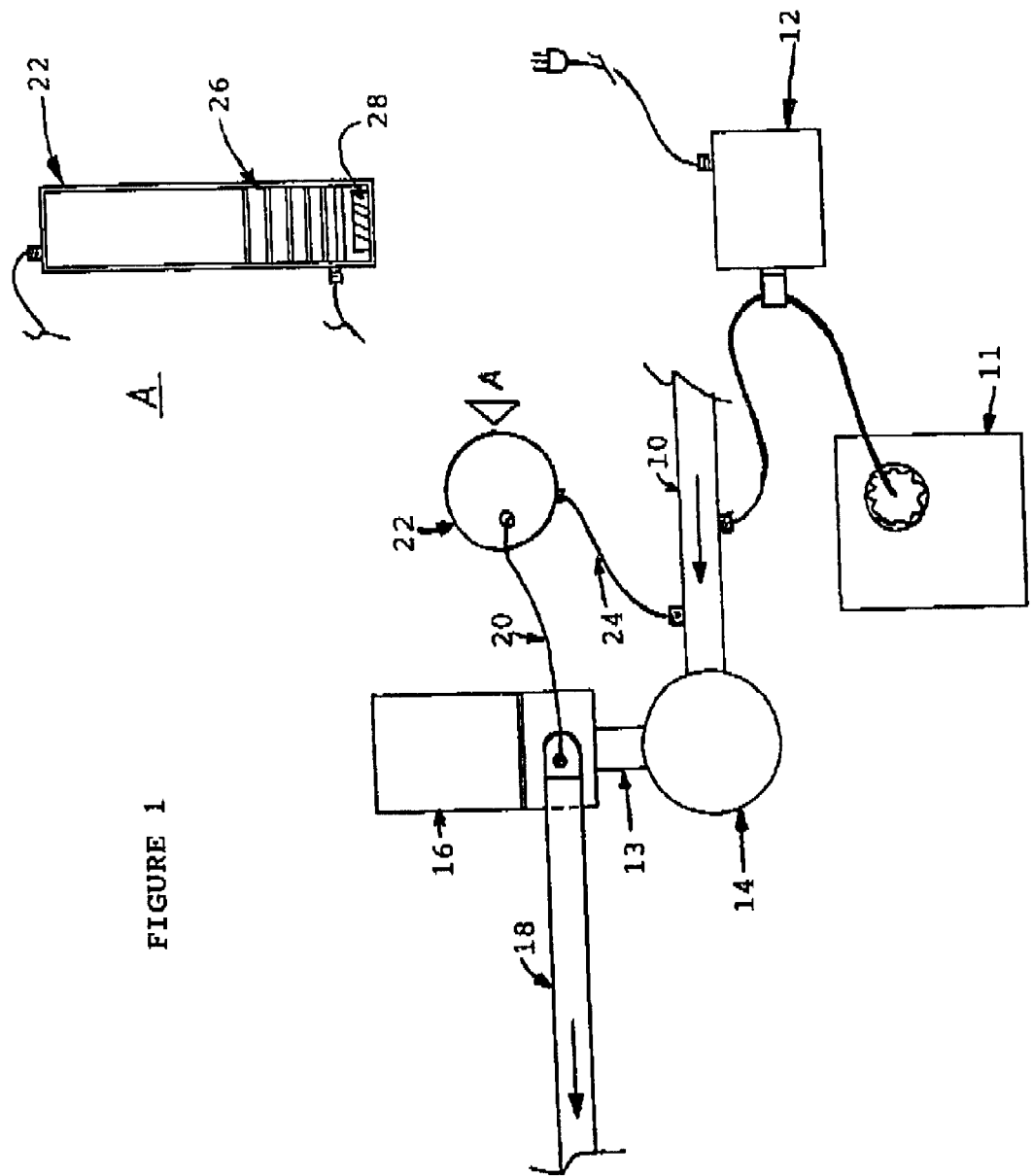
FIG. 1 shows a schematic view of apparatus for a water sanitisation process in accordance with the invention.

Referring to the drawings, an inlet stream of water to be sanitised is drawn into inlet conduit 10 by a pumping suction action and reagents are delivered directly into the flow. Hydrogen peroxide is delivered from a source of concentrated reagent 11 (for example 50% w/w) by means of a solenoid valve or timer-controlled metering pump 12 operated intermittently. Such an arrangement maintains a level of hydrogen peroxide in the water preferably between 10 and 50 ppm. It has been found experimentally that regular dosing at short intervals is far more effective for controlling disease-causing organisms than dosing at long intervals, by providing the water with a continuous minimum concentration of reagent to ensure that the water is always "oxygenated".

The water flow in inlet conduit 10 then passes through coarse filter 14 to remove coarse particles of solids, leaves or other detritus from the pool system. The water flow then passes through pipe 13 and into the main water reticulation pump 16 itself. The pump then returns the majority of the water flow to the body of water being sanitised by means of outlet conduit 18. A sidestream of water, however, from pump 16 is delivered by means of feed conduit pipe 20 to flow through container 22 before being returned into inlet conduit pipe 10 downstream from the injection point of hydrogen peroxide reagent by means of return conduit pipe 24. In use, this sidestream flow of water has further important sanitisation reagents delivered to it by means of container 22.

Within container 22 there exists a main containment area for pelletised or disc-like solid sources of chlorine reagent 26. Such an arrangement delivers chlorine to the body of water to be sanitised at a rate of between 0.4 and 0.8 ppm. No hazardous chlorination by-products will form since the available chlorine or other halogen will react immediately with the available hydrogen peroxide and form hypochlorous acid, as, for example, in the case of chlorine addition.

Within container 22 there exists a plurality of metallic bars or other shaped source of copper and silver metal (for example rods or granules), indicated as 28 in the illustration. The copper source may be present in a combined metallic form (eg with zinc as brass) not necessarily of any particular grade or purity. Such an arrangement ensures that when hydrogen peroxide and halogen are present in the body of water to be sanitised, and this liquid is combined with metallic copper and silver, there is a synergistic action which occurs. The release of small amounts of these metals as colloidal material occurs in a controlled-rate dissolution by the action of the peroxide oxidising agent. Colloidal silver and copper is very safe for contact with human beings and has FDA approval.

As described in prior art, the amount of hydrogen peroxide used ensures that all halogen is converted to hypochlorous acid and sufficient hydrogen peroxide is left over to oxygenate the water. The colloidal particulate silver and copper co-present in the water to be sanitised act as a catalyst for the conversion of some of the hydrogen peroxide to hydroxyl ion radicals and oxygen which also provide means to sanitise bacteria and other organisms where present. Hydroxyl radicals are the most aggressive free radicals known to medical and biological science and, in separate experiments, have been shown to achieve almost complete destruction of certain types of bacteria present in very short times.

Additionally, silver is also known for its anti-bactericidal properties and copper is also known to be a good algaecide and a potent anti-fungal reagent.

There is no particular preferred orientation of container 22, whether vertical or horizontal, nor do the metallic sources of copper and silver metal, indicated as 28 in the illustration, need to be placed at one end of container 22. The container 22 merely provides a zone of intimate mixing between the water containing hydrogen peroxide and chlorine, and a zone where metals undergo a controlled-rate dissolution to form colloidal metal material.

The water which flows through container 22 exits via a return conduit 24 which may be connected to any position on either the inlet conduit 10 or the outlet conduit 18, provided that when in use, water under sufficient pressure from the pump 16 can pass in sequence through the feed conduit 20, the container 22, and the return conduit 24. The other requirement during operation is that the hydrogen peroxide reagent 11 should pass into the flow of water in the inlet conduit 10 at a position upstream of the connection of the feed conduit 20 to the outlet conduit 18.

In one experiment, we have shown that by using the mixed-oxidant and metals system illustrated in FIG. 1 (iii), we are able to achieve a significant reduction in bacterial count when comparing the results to those made using (i) a halogen (chlorine) system alone and (ii) a halogen (chlorine) and hydrogen peroxide mixed oxidant system. System (ii) and system (iii) operated at 226 mV ORP which is within the preferred operating range of redox potential (ORP) for water to be sanitised of 220–290 mV, indicating that the correct relative amounts of hydrogen peroxide and halogen were present. The results are illustrated graphically in FIG. 2. From the data it can be seen that from an initial bacteria count of 441, the untreated control sample bacteria count rose to 508 by the end of the 1 hour long experiment. The system which sanitises water using a halogen (chlorine) system alone gave a final bacteria count of 398 (effectively a 22% reduction in bacteria). The system which uses a halogen (chlorine) and hydrogen peroxide mixed oxidant system gave a final bacteria count of 288 (effectively a 43% reduction in bacteria). Finally, the system which uses a halogen (chlorine) and hydrogen peroxide mixed oxidant system in combination with copper and silver metals as defined by this invention, gave a final bacteria count of 270 (effectively a 47% reduction in bacteria).

Previously it has not been appreciated that a water sanitisation process involving hydrogen peroxide and halogen could be augmented by the catalytic properties or colloidal metals, wherein the process is carried out in a newly designed apparatus which can contain the reagents in close proximity to one another and provide some enhanced health and safety benefits to operators and users of the body of water being sanitised.

What is claimed is:

1. A method of sanitising a body of water by:
   (a) adding an amount of hydrogen peroxide predetermined by the volume of water to be sanitised, and
   (b) adding an amount of halogen predetermined by the volume of water to be sanitised, and
   (c) adding an amount of one or more of the group comprising silver and copper as colloidal dissolved metals produced by the controlled dissolution of the corresponding metallic source metals under the action of hydrogen peroxide and halogen present in the water to be sanitised, and
   wherein the amount of hydrogen peroxide is so predetermined to ensure that all halogen is converted to hypohalous acid and sufficient hydrogen peroxide is left over to provide at least some oxygenation of the water.

2. A water sanitisation method as claimed in claim 1 including the use of a reticulation pump for providing a flow of water requiring sanitisation, and a container arranged to receive water under pressure from said pump, said container being adapted to contain sources of said colloidal dissolved metals and halogen reagent, whereby said water is recirculated through said container and returned to the flow of water, and wherein, upstream from where said container receives water from said pump, metering means are arranged to deliver hydrogen peroxide reagent into the flow of water.

3. A water sanitisation method as claimed in claim 2 wherein said water is returned to the flow of water downstream of the delivery of hydrogen peroxide reagent into the flow of water.

4. A water sanitisation method as claimed in claim 2 wherein the flow of water to said container from the pressure side of the pump is regulated by constriction in order to allow an appropriate residence time of fluid in the container for effective chemical reactions to occur.

5. A water sanitisation method as claimed in claim 2 wherein the rate of hydrogen peroxide reagent delivery is adjusted to suit the particular conditions of sanitisation required and the flow rate of water for treatment.

6. Apparatus for sanitising a flow of water recirculated from a body of water by a pump having an inlet conduit and an outlet conduit both in communication with the body of water, said apparatus comprising a container adapted to hold sources of one or more of the group comprising silver and copper as colloidal dissolved metals and a source of halogen reagent, a feed conduit extending from the container and adapted to be connected to the outlet conduit, a return conduit adapted to be connected to one of the inlet conduit and the outlet conduit, such that in use water under pressure from the pump passes through the feed conduit, the container, and the return conduit, said apparatus further comprising metering means adapted to deliver hydrogen peroxide reagent into the flow of water upstream of the connection, of the feed conduit to the outlet conduit.

7. Apparatus for sanitising water as claimed in claim 6 wherein said metering means comprises a solenoid valve or metering pump or the like, adapted to deliver hydrogen peroxide reagent at a pre-determined rate into the flow of water upstream of the pump.

8. Apparatus for sanitising water as claimed in claim 5 wherein the pump is associated with a coarse filter, wherein the return conduit is connected to the inlet conduit upstream of the coarse filter.

9. Apparatus for sanitising water as claimed in claim 5 wherein the container is adapted to include sources of metallic copper and silver and halogen reagent in which the metallic copper and silver are present as a plurality of metallic bars, rods or granules, and sources of chloride are present in solid form.

* * * * *